(12) United States Patent
de Paiva Bueno et al.

(10) Patent No.: US 11,802,824 B2
(45) Date of Patent: Oct. 31, 2023

(54) TEST ARRANGEMENT AND METHOD FOR TESTING BREAKAGE AND MECHANICAL PROPERTIES OF ROCK PARTICLES

(71) Applicant: OULUN YLIOPISTO, Oulu (FI)

(72) Inventors: Marcos de Paiva Bueno, Oulu (FI); Janne Torvela, Oulu (FI); Rajiv Chandramohan, Oulu (FI)

(73) Assignee: GEOPYÖRÄ OY, Oulu (FI)

( * ) Notice: Subject to any disclaimer, the term of this patent is extended or adjusted under 35 U.S.C. 154(b) by 500 days.

(21) Appl. No.: 17/257,367

(22) PCT Filed: Feb. 18, 2020

(86) PCT No.: PCT/FI2020/050100
§ 371 (c)(1),
(2) Date: Dec. 31, 2020

(87) PCT Pub. No.: WO2020/136309
PCT Pub. Date: Jul. 2, 2020

(65) Prior Publication Data
US 2021/0270709 A1 Sep. 2, 2021

(51) Int. Cl.
*G01N 3/08* (2006.01)
*B02C 4/02* (2006.01)
(Continued)

(52) U.S. Cl.
CPC .............. *G01N 3/08* (2013.01); *B02C 4/02* (2013.01); *B02C 4/32* (2013.01); *B02C 4/42* (2013.01);
(Continued)

(58) Field of Classification Search
CPC .......... G01N 3/08; G01N 3/068; G01N 33/22; G01N 33/24; G01N 2203/0019;
(Continued)

(56) References Cited

U.S. PATENT DOCUMENTS

| 5,392,633 A | 2/1995 | Morris |
| 2013/0277467 A1 | 10/2013 | Niklewski |
| 2022/0412854 A1* | 12/2022 | Schoen ................. E21B 49/003 |

FOREIGN PATENT DOCUMENTS

| WO | 2007/134367 | 11/2007 | |
| WO | 2017/064562 | 4/2017 | |
| WO | WO-2021062556 A1 * | 4/2021 | ............... G01N 3/10 |

OTHER PUBLICATIONS

International Search Report for PCT/FI2020/050100, dated Jun. 5, 2020, 4 pages.
(Continued)

*Primary Examiner* — Jonathan M Dunlap
(74) *Attorney, Agent, or Firm* — Lucas & Mercanti, LLP

(57) ABSTRACT

The invention relates to a test arrangement for testing breakage and mechanical properties of rock particles. Test arrangement comprises a support (1, 2) and two counter-rotatable crushing rolls (3, 3') supported on the support (1, 2) and a drive arrangement (M1, M2) for rotating the crushing rolls (3, 3'). Crushing rolls (3, 3') are facing each other and defining therebetween an input gap (G) for the rock particles, said rolls being arranged to crush rock particles (RP) to smaller daughter particles (DP). Test arrangement comprises a force measurement arrangement (7, 7') for determining the compressive strength of rock particles (RP). Force measurement arrangement (7, 7') being coupled to a processor (PR) comprised by the test arrangement. The processor (PR) being arranged to calculate the breakage force applied to each rock particle (RP) over time. The test arrangement (TA) further comprises an energy measurement arrangement (5, 5') for measuring information relating to energy applied to each rock particle (RP), said energy measurement arrangement (5, 5') being coupled to said processor (PR), said processor (PR) being arranged to calculate energy applied to each rock particle (PR).

16 Claims, 2 Drawing Sheets

(51) Int. Cl.
*B02C 4/32* (2006.01)
*B02C 4/42* (2006.01)
*G01N 33/22* (2006.01)
*G01N 3/06* (2006.01)
*G01N 33/24* (2006.01)

(52) U.S. Cl.
CPC ............ *G01N 3/068* (2013.01); *G01N 33/22* (2013.01); *G01N 33/24* (2013.01); *G01N 2203/0019* (2013.01); *G01N 2203/0037* (2013.01); *G01N 2203/0087* (2013.01); *G01N 2203/0284* (2013.01); *G01N 2203/0641* (2013.01)

(58) Field of Classification Search
CPC ... G01N 2203/0037; G01N 2203/0087; G01N 2203/0284; G01N 2203/0641; B02C 4/02; B02C 4/32; B02C 4/42; B02C 4/48; B02C 25/00
See application file for complete search history.

(56) References Cited

OTHER PUBLICATIONS

Written Opinion of the ISA for PCT/FI2020/050100, dated Jun. 5, 2020, 7 pages.
Daniel et al., "HPGR model verification and scale-up", Minerals Engineering, vol. 17, 2004, pp. 1149-1161.

\* cited by examiner

TEST ARRANGEMENT AND METHOD FOR TESTING BREAKAGE AND MECHANICAL PROPERTIES OF ROCK PARTICLES

This application is the U.S. national phase of International Application No. PCT/FI2020/050100 filed 18 Feb. 2020, which designated the U.S., the entire contents of which is hereby incorporated by reference.

BACKGROUND

Orebodies are intrinsically variable in composition and physical properties by the virtue of their heterogeneous nature. There are few orebodies that consist of one single lithology or any other geological classification (ore types). This variability is usually evident from orebody characterization programs by showing the spatial distribution of these properties. Orebody complexity is well recognized, however, the design of most processing plants is still performed using fixed or discrete values of the orebody properties as input parameters. Designing a process plant has many conventions and one of these is that selecting the 80th percentile value of a key measure, such as the JK (Julius Kruttschnitt) drop weight test (JKDWT) A*b parameter, discussed in Napier-Munn, T. J., Morrell, S., Morrison, R. D. & Kojovic, T. (2005): Mineral comminution circuits: their operation and optimisation, Julius Kruttschnitt Mineral Research Centre, (JKMRC).

JKDWT and other drop-weight tests use nominal energy (E=m×g×h, were m is weight, g is gravity constant and h is the dropping height).

Also known is SMC Test® drop weight test index (DWI), discussed in: Morrell, S. (2004): Predicting the specific energy of autogenous and semi-autogenous mills from small diameter drill core samples. Minerals Engineering, 17 (2004):447-451.

Also known is SAG power index (SPI®), discussed in Starkey J. & Dobby, G. (1996): Application of the Minnovex SAG Power Index at five Canadian SAG plants, in Mular, A. L., Barratt, D. J. and Knight, D. A. (Eds.): Proceedings of the International Conference on Autogenous and Semi-Autogenous Grinding Technology (pp. 345-360). Vancouver: University of British Columbia (UBC).

Also known is Bond ball mill work index, (BWI), discussed in Bond, F. C. (1961): Crushing & grinding calculations part I, British Chemical Engineering, 6:378-385.

The above mentioned technology may provide unquestionable margin of design safety in the plant. However, this approach does not consider the inherent variability of the orebody and, therefore, can lead to results which are not representative for some of the ore types.

The design of comminution circuits for the treatment of hard rock involves the process of sample selection, test work, data analysis and data modelling/interpretation. However, over the past couple of years several issues have arisen due to ore variability. The impact of these issues on project viability is generally more pronounced when treating ores harder than average to soft ores due to the greater impact on capital and operating costs.

Mining companies tend to invest more in understanding resources than in understanding metallurgy, of which comminution testing is a key component. If the test work program is not adequately executed and interpreted, there are risks of establishing wrong design criteria and compromising the final design. One consequence of this is that several projects have underperformed and have resorted to spending additional capital to mitigate the problem (e.g. secondary crushing, high intensity blasting and/or barren pebble rejection). Another consequence is that some financiers are expressing less confidence in designer's ability to predict the performance of grinding circuits and this has impacted on the ability of companies to obtain funding.

Comminution tests are clearly an important element in the proper design of ore beneficiation plants. Traditionally, test work has been conducted with a few representative reference samples. For geometallurgical modelling the entire ore body is explored to understand the variability within the resource and to establish spatial geometallurgical domains that show the differential response to mineral processing. Setting up a geometallurgical program for an ore deposit requires extensive test work. Methods for testing the comminution behaviour must therefore be more efficient in terms of time and cost but also with respect to sample requirements. The integration of the test method into the geometallurgical modelling framework is also important.

Geometallurgical mapping/modelling is needed for finding out the properties of ore bodies or other rock bodies or particles thereof. For this purpose, rock particles are subjected to breakage characterization test.

Breakage characterization test can give useful information regarding features of the rock bodies and regarding designing of the process equipment such as comminution devices of the mining industry processing plant. Deeper knowledge regarding rock breakage properties would be highly advantageous because more than 50% of the energy consumed in mining is consumed in comminution, compared to only 10% in excavation.

Different techniques have been developed to assess the breakage characteristics of rocks and generate the parameters for modelling. The pioneering procedure was the twin pendulum test, discussed in Narayanan, S. S.; Whiten, W. J: Determination of comminution characteristics from single particle breakage tests and its application to ball mill scale-up, published in: Trans. Inst. Min. Metall. Sect. C Miner. Process. Extr. Metall. 1988, 97, C115-C124.

Twin pendulum test was later replaced by the JK drop weight tester (JKDWT, JK is referring to Julius Kruttscnitt).

The already mentioned Morrel-document (Morrell, S. (2004): Predicting the specific energy of autogenous and semi-autogenous mills from small diameter drill core samples. Minerals Engineering, 17 (2004):447-451) introduced the SMC test that uses the above mentioned JKDWT device and a different procedure that aimed to simplify the test. As an attempt to make procedure slightly faster, the JK rotary breakage tester (JKRBT), shown in document WO2007134367, was developed, it is relying on a different breakage mechanism. More recently, document WO2017064562 (Kojovic, T.) introduced HIT-device which is a further simplification of the JKDWT device.

These tests use devices that can break single particles of different sizes at different specific energy levels, Ecs (kWh/t). The product size distributions are then used to define the degree of breakage called $t_{10}$ (the percentage passing one tenth of the original size) for the different energies applied. Although the well-established breakage test procedures and test devices provide some reasonable estimation of rock strengths, these test methods have limitations. These limitations rely on the assumption that all applied energy to the rock particle use entire energy for breakage. However, this is not true, and the actual energy absorbed by the particle vary depending on the rock physical properties. It has been observed that secondary breakage has significant effect to the degree of breakage, therefore affecting the $t_{10}$ parameter (fragmentation). This effect is heavily machine dependent, so varies between types of tests. The newly developed JKRBT faces no exception.

The ultra-fast load cell developed at Utah University aims to quantify the peak strength required to cause the first fracture. This method of quantifying strength of rock fundamentally is discussed in: Bourgeois, F., et al. (1992). Low-impact energy single-particle fracture. Comminution: theory and practice. S. K. Kawatra. Littleton, Society for Mining, Metallurgy, and Exploration: 99-108.

Another document: "Measurement of fracture energy during single-particle fracture." Minerals Engineering 6(4): 353-367, has provided some quality data, however the experimental procedure is considered to be slow when compared to the rapid characterisation capabilities of the JKRBT for example.

Instrumented crushers using a double roll mechanism to measure particle strength of non-rock materials are shown in U.S. Pat. No. 5,392,633 "Measuring the strength of abrasive grains" and document: J. N. Brecker: "The fracture strength of the of abrasive grains" (November 1974) in Journal of Engineering, pages 1253-1257. A similar device used in rock breakage application is shown in: Lieberwirth H., et. al.: "Dynamics in double roll crushers" in publication Mineral engineering (2016) This device has been used to study the forces present in the crushing equipment itself more so than the properties of the particles being crushed.

In summary, drop-weight tests (DWT) devices require laborious procedures and use nominal energy levels. Use of nominal energy levels is inaccurate, while the previously known instrumented double roll crushers do not have suitable instrumentation and other elements to make the known arrangements good enough for reliable and accurate rock breakage characterization tests.

BRIEF DESCRIPTION

An object of the present invention is to provide a test arrangement to solve or to alleviate the above disadvantages. The purpose of the invention is to enable fast and low-cost rock particle testing in a wide range of sizes. The characterization intends to measure the compressive strength and the actual total energy absorbed by each particle. The absorbed energy is then related to the progeny produced from the parent particle.

The objects of the invention are achieved by a test arrangement and method which are characterized by what is stated in the independent claim. The preferred embodiments of the invention are disclosed in the dependent claims.

An advantage of the disclosed test arrangement and method is that it is able to accurately produce extensive rock compressive strength and breakage characterization data, while still being able to remain fast and suitable for online low-cost testing.

BRIEF DESCRIPTION OF THE DRAWINGS

In the following the invention will be described in greater detail by means of preferred embodiments with reference to the accompanying drawings, in which.

DETAILED DESCRIPTION

Figure 1:
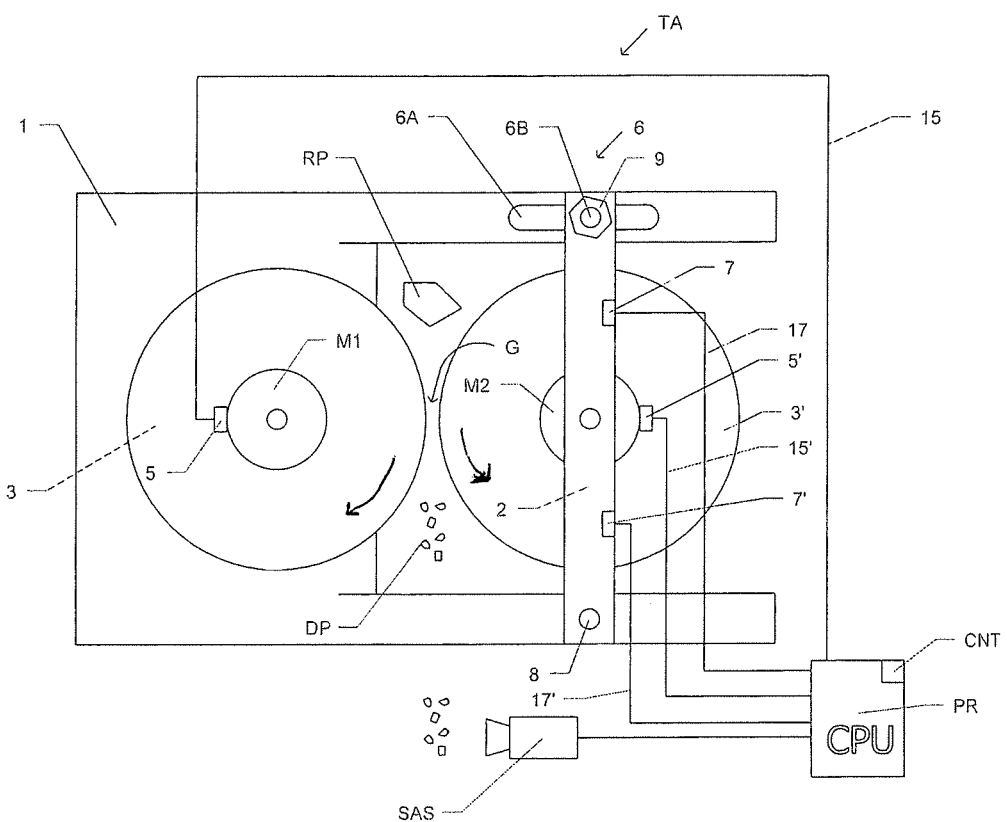
FIG. 1 shows test arrangement

Referring to FIG. 1, there is shown test arrangement TA for testing breakage properties of rock particles RP, said test arrangement comprising a support 1, 2 and two counter-rotatable crushing rolls 3, 3' (wheels) supported on the to support 1, 2. Support 1 for first roll 3 can be seen as a rigid frame and support 2 for second roll 3' is a movable vertical beam or other support 2 that can be moved, thanks to adjustment mechanism 6 having a slot 6A and element 6B such as bolt, at the support frame 1 and an element such as nut 9 (on the bolt 6A) arranged to press horizontally movable support beam 2 against frame 1. Support beam 2 with related second roll 3' can be horizontally moved in relation to support 1 and in relation to first roll 3. This second support 2 supporting the second roll 3' is movable so that the width of the input gap G between the rolls 3, 3' can be adjusted. Similar or different adjustment mechanism 8 can also be at the lower end of the support beam 2.

The adjustment mechanism 6 or 8 can also been seen as a hinge or a part of the hinge, intended for protection purposes. Relating to that, if the force caused by the crushed particle exceeds the friction produced by pressing the support beam 2 against the support frame 1, then the support beam 2 may rotate around the part 8 (adjustment mechanism/hinge) to allow the second roll (wheel) 3' to escape and relieve the force, as a protection mechanism against excessive loading.

During the operation of the arrangement, the gap adjustment mechanism is locked and the upper and lower ends of the support beam 2 do not move. End of the support beam 2 is pressed/clamped against the support frame 1 so that the friction between the parts prevents the support beam 2 (carrying the second roll 3') from moving.

Rock particles RP enter the gap G between the parallel rolls 3, 3'. Arrangement comprises force measurement arrangement 7, 7' for measuring the breakage force of the rock particles RP. Force is measured from the forceful bending (caused by rock particle RP between the rolls 3, 3') of the support beam 2, support beam 2 is locked to its place at both ends of the support beam 2.

One or both ends of the beam 2 could be hinged against the frame 1 after the gap adjustment is fixed in place. Both the rotation and the horizontal movement of the end of the support beam 2 in relation to the support frame changes the bending behaviour of the beam 2, this which can be taken into account by software calibration.

In an embodiment, the force measurement arrangement 7, 7' comprises to one or more strain gauges, sensing the bending deformation of the vertical support beam 2. The support beam 2 (carrying the second roll 3') and the related strain gauges together form a load cell. In an embodiment and as an example only, a suitable strain gauge can be Kyowa KFG-5-120-C1-11L3M3R. Other means of measuring the bending of the support beam 2 are possible, too. The force measurement arrangement 7, 7' is to measure information relating to the rock particle compressive strength, said force measurement arrangement 7, 7' being coupled via lines 17, 17' to a processor PR, said processor PR being arranged to calculate the breakage force applied to each rock particle RP over time.

Crushing rolls 3, 3' i.e. comminution rolls i.e. rotatable crushing elements can be narrow wheels, having narrow axial width of for example 25-50 mm, and diameter of for example 20-80 cm. One possible material for rolls 3, 3' is metal, such as hardened steel. An example of the weight of each roll 3, 3' is 10-100 kg, such as 40-60 kg, this depends on the required maximum available energy.

Additionally, test arrangement TA comprises a drive arrangement M1, M2 for rotating the crushing rolls. Drive arrangement can be electric motors M1, M2. As an example only, suitable power rating for electric motors is 50-100 W.

Crushing rolls 3, 3' are facing each other and they define therebetween an input gap G for the rock particles RP, said rolls 3, 3' being arranged to crush/comminute rock particles to smaller daughter particles DP (progeny). Test arrangement is arranged to receive only one rock particle at the time to be inputted to input gap between the rolls 3, 3'.

Width of the gap G is adjusted to be less than the size (minimum diameter) of the inputted rock particle RP. In an example, width of the gap G is percentage (⅓ to ⅔) of the average particle size (diameter). Particle size can range from 8 mm to 40 mm.

The test arrangement TA further comprises an energy measurement arrangement 5, 5' for determining compressive strength of rock particles, said energy measurement arrangement 5, 5' being coupled to said processor PR via lines 15, 15', said processor PR being arranged to calculate energy applied to each rock particle RP over time.

Word "processor" is to be understood widely, it can be microprocessor (CPU), computer or some other suitable element, and it can be an integral unit, or it can have several related but possibly detached elements such as discrete components.

Processor PR includes, or has access to, data which contains the relationship of the measured feature (strain, speed) and the calculation output (compressive strength, breakage energy).

Regarding the corresponding method, the method is a method for testing breakage properties of rock particles. The method comprises: weighing the rock particles mass, inputting rock particles between two counter rotating crushing rolls 3, 3' for crushing rock particles to smaller daughter particles, accomplishing (performing, carrying out) a force measurement for measuring information relating to the breakage force applied to each rock particle RP, accomplishing (performing, carrying out) an energy measurement for measuring information relating to energy applied to each rock particle (RP), calculating breakage force applied to each rock particle (RP), and calculating energy applied to each rock particle PR. The weight of the rock particles can be measured with a suitable weighing device and the weight value can be transferred/inputted to the processor PR.

In an embodiment, the energy measurement arrangement 5, 5' is an arrangement for measuring the energy loss of the rotatable rolls 3, 3' during the breakage event of each rock particle RP. Rock particle RP between the rolls 3, 3' will slow down the speed (and rotational moment) of the rolls 3, 3', and the amount of loss of speed (and loss of rotational moment) refers to amount of energy loss, which in turn refers to amount of energy given from counter-rotating rolls to the rock particle RP. Regarding the corresponding method, in an embodiment the method is such that energy loss of the rotatable rolls 3, 3' during the breakage event of each rock particle is measured.

In a further embodiment, the energy measurement arrangement 5, 5 comprises sensor structure, said sensor structure being arranged to measure from the rolls 3, 3' one or more of the following: speed, angular velocity, rotational position. Sensor structure may comprise optical rotary encoder, having a hoop with a gear-like pattern of teeth, which are measured by an infrared optical gate of the type TCST-1103, mentioned as an example only.

In the embodiment shown in FIG. 1, the motor is integrated directly to the respective roll (wheel). In a possible variation where the motor is not directly attached to the roll (wheel), torque may be measured from the intermediate shaft. Torque may also be measured from reaction forces or torques applied by the motor against the frame. The torque produced by the motor signals energy transfer between the motor and the wheel, not directly between the wheel and the rock particle. In an embodiment, it is possible to measure energy indirectly by observing the torque that the motor applies to the roll (wheel). The amount of torque measured depends on how the motor reacts to the loss of angular velocity of the roll (wheel)—in other words, how much torque for how many revolutions over what time is required to bring the roll (wheel) back to the starting speed.

Regarding breakage events, in a typical breakage event, there is a sharp peak of force when the rock particle enters the gap and touches both wheels, followed by a short sustained plateau of force as the pieces of the rock are reduced further in size, and then a short taper off as the remaining pieces exit the gap. The highest forces measured are typically at the beginning of the breakage event with the initial breakage across the whole cross-section area of the particle. This follows approximately the relationship of Stress=Force/Area, where the stress required to break the particle depends on the material (ideally), so the amount of force required to break a particle or a fragment becomes less when the cross-section area of the particle or fragment of a particle becomes smaller. The smaller the gap is in relation to the original particle size, the more the particle has to break down to fit through it. This means more force must be sustained for a longer time, and more energy is spent.

In order to get more reliable measurement data from force measurement sensors 7, 7' and from energy measurement sensors 5, 5', in an embodiment the test arrangement TA comprises a controller CNT for controlling the drive arrangement M1, M2, for disabling and/or limiting the drive arrangement M1, M2 regarding rotating the crushing rolls, in order to create interference free conditions for the measurement operations during breakage events. In an embodiment. the power supply to the motors M1, M2 is stopped to allow free rotation. The motor will keep revolving with the roll (wheel). A non-integrated drive configuration may also be mechanically separated by a mechanism, such as a clutch or a ratchet to remove the influence of the motor from the wheel. In any case, the crushing rolls 3, 3' will keep on rotating since the rolls 3, 3' still have rotational kinetic energy.

Regarding the corresponding method, in an embodiment the method is such that drive arrangement M1, M2 of the rolls is disabled and/or limited regarding rotating the crushing rolls, in order to create interference free conditions for the measurement operations during breakage events.

Figure 2:
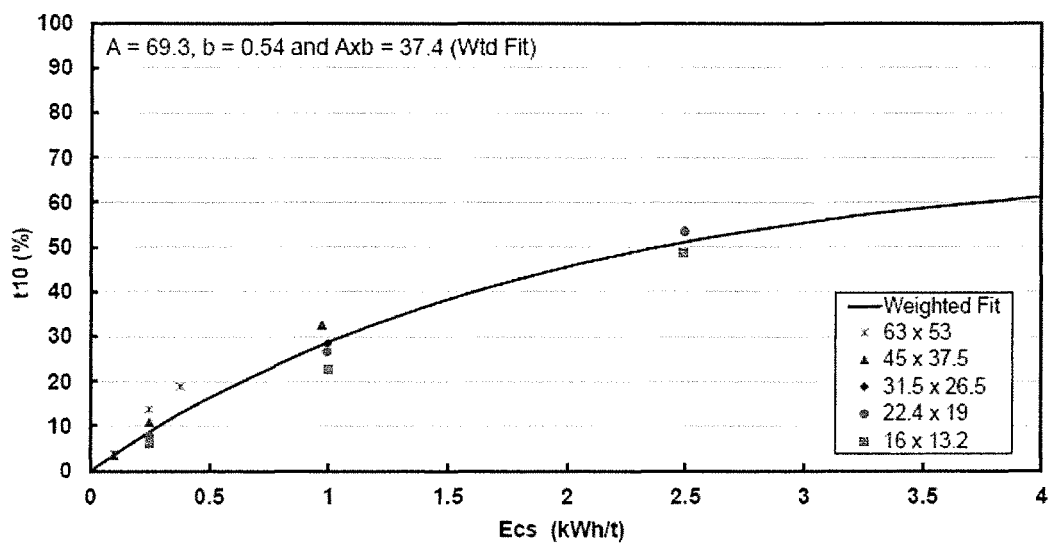
FIG. 2 shows the dependency of $t_{10}$ %-value and specific breakage energy

FIG. 2 shows the dependency of $t_{10}$ %-value and specific breakage Energy Ecs. In FIG. 2 horizontal axis represents special (=per unit of mass) breakage energy Ecs shown in kWh/t (kilowatt hours/ton). The curve shown in FIG. 2 is represented by the equation: $t_{10}=A*(1-e^{-b*Ecs})$, where ore specific parameters A and b are generated by least squares fitting to the breakage test data. Ecs represents specific breakage energy and "e" is irrational and transcendental number approximately equal to 2.718281828459. Referring to FIGS. 1-2, in an embodiment, the test arrangement TA further comprises or allows (enables connection) use of a particle size analysis system SAS for measuring the size of the daughter particles DP fee falling after being broken between the crusher rolls (3, 3'), so as to determine the particle size distribution (PSD) and degree of breakage $t_{10}$. This $t_{10}$ value is the % passing 1/10 of the original size of the particle. Alternatively, the PSD and/or $t_{10}$ can be determined separately through mechanical sieving. One example of a size analysis system SAS is an optical detecting system such as a camera, coupled to the processor PR.

Referring to above, in an embodiment, the size analysis system SAS is coupled to said processor PR, and said processor PR is arranged to determine the correlation between degree of breakage and measured breakage force and/or the correlation between degree of breakage and measured energy applied to each rock particle RP. Regarding the corresponding method, in an embodiment the method is such that the method comprises determining correlation between degree of breakage and measured breakage force and/or correlation between degree of breakage and measured energy applied to each rock particle RP.

Test arrangement TA is arranged to determine the compressive strength of the tested material (rock particles RP).

The test arrangement is arranged to determine the breakage-energy relationship of the tested material i.e. rock particles RP, reference is made to FIG. 2, where horizontal axis represents special (=per unit of mass) breakage energy shown in kWh/t (kilowatt hours/ton). Regarding the corresponding method, in an embodiment the method is such that breakage-energy relationship of the rock particles (RP) in determined in the method.

It will be obvious to a person skilled in the art that, as the technology advances, the inventive concept can be implemented in various ways. The invention and its embodiments are not limited to the examples described above but may vary within the scope of the claims.

The invention claimed is:

1. Test arrangement for testing breakage and mechanical properties of rock particles, said test arrangement comprising:
a support;
two counter-rotatable crushing wheels supported on the support;
a drive arrangement for rotating the crushing wheels, said crushing wheels facing each other and defining therebetween an input gap for the rock particles, said wheels being arranged to break the rock particles to smaller daughter particles;
wherein the test arrangement is arranged to receive only one rock particle at a time to be inputted to the input gap for breakage testing;
an energy measurement arrangement arranged to measure information relating to energy absorbed by the rock particles during the breakage; and
a processor coupled to the energy measurement arrangement and arranged to receive, as inputs, at least one degree of breakage of the rock particles as a result of the breakage and the corresponding breakage energies absorbed by the rock particles during the breakage, to determine a correlation between the degree of breakage and the breakage energies, and to output the correlation.

2. Test arrangement according to claim 1, wherein the energy measurement arrangement is an arrangement for measuring the energy loss of the rotatable wheels during the breakage event of each rock particle.

3. Test arrangement according to claim 2, wherein the energy measurement arrangement comprises a sensor structure, said sensor structure being arranged to measure speed and/or angular rotational position of the wheels.

4. Test arrangement according to claim 1, wherein the test arrangement comprises a controller for controlling the drive arrangement, for at least one of disabling and limiting the drive arrangement regarding rotating the crushing wheels, in order to create interference free conditions for the measurement operations during breakage events.

5. The test arrangement according to claim 1, wherein the degree of breakage comprises a $t_{10}$-value representing %-value of material passing 1/10th of the original particle size.

6. The test arrangement according to claim 1, further comprising a feeder configured to feed the rock particles to the input gap such that only one rack particle at a time is input to the input gap.

7. The test arrangement according to claim 1, wherein the processor is configured to receive, as a further input, a mass of each rock particle before the rock particle is input to the input gap, to compute a specific breakage energy for each rock particle on the basis of the mass and the measured breakage energy.

8. The test arrangement according to claim 1, wherein the drive arrangement comprises a gearless motor.

9. The test arrangement according to claim 1, further comprising the processor is configured to compute at least one size specific energy and at least one grindability parameter on the basis of a stored correlation between the at least one grindability parameter and the size-specific energy.

10. The test arrangement according to claim 1, further comprising a force measurement arrangement arranged to determine compressive strength of each of the rock particles during the breakage, wherein the processor is coupled to the force measurement arrangement and configured to receive, as a further input, the compressive strength and to compute at least one parameter representing compressive strength of the rock particles.

11. Method for testing breakage properties of rock particles, comprising:
weighing the rock particles' mass;
inputting the rock particles between two counter rotating crushing wheels to break the rock particles to smaller daughter particles such that said rock particles are input between the crushing wheels one at a time for said breakage;
accomplishing an energy measurement for measuring information relating to energy absorbed by each rock particle;
determining at least one degree of breakage of the rock particles resulting from the breakage;
calculating, by a processor on the basis of the degree of breakage and the corresponding breakage energies measured by the energy measurement a correlation between the degree of breakage and the breakage energies, and
outputting, by the processor, the correlation.

12. The method according to claim 11, wherein the energy measurement is measured energy loss of the rotatable wheels during the breakage event of the rock particles.

13. The method according to claim 11, wherein said weighing is performed by a scale coupled to the processor.

14. The method according to claim 11, further comprising:
accomplishing a force measurement to determine compressive strength of each of the rock particles during the breakage,
computing, by the processor on the basis of the force measurement, at least one parameter representing compressive strength of the rock particles.

15. The method according to claim 11, wherein the drive arrangement of the wheels is disabled and/or limited regarding rotating the crushing wheels during the breakage, in order to create interference free conditions for the measurement operations during the breakage.

16. The method according to claim 11, wherein the processor computes a specific breakage energy for each rock particle on the basis of the mass and the measured breakage energy of said each rock particle, and further computes a grindability parameter on the basis of the specific breakage energy.

* * * * *